United States Patent [19]

Wheeler et al.

[11] Patent Number: 4,839,188

[45] Date of Patent: Jun. 13, 1989

[54] STABILIZED FAT COMPOSITIONS

[75] Inventors: Edward L. Wheeler, Watertown; Robert J. Franko, Beacon Falls, both of Conn.

[73] Assignee: Uniroyal Chemical Company, Inc., Middlebury, Conn.

[21] Appl. No.: 199,989

[22] Filed: May 27, 1988

[51] Int. Cl.$^4$ .................. A23D 5/04; C07D 251/70
[52] U.S. Cl. ............................ 426/545; 260/398.5; 426/601; 426/643; 426/654; 544/197
[58] Field of Search .............. 426/541, 545, 601, 654, 426/643; 544/197; 260/398.5

[56] References Cited

U.S. PATENT DOCUMENTS

| 3,414,570 | 12/1968 | Coburn | 544/197 |
| 3,706,740 | 12/1972 | Dexter | 426/545 |
| 3,709,884 | 1/1973 | Dexter et al. | 426/545 |
| 3,905,939 | 11/1975 | Dexter et al. | 426/545 |
| 4,085,282 | 4/1978 | Jones | 544/197 |
| 4,692,544 | 9/1987 | Goerner | 260/398.5 |

FOREIGN PATENT DOCUMENTS

| 0202611 | 11/1986 | European Pat. Off. | 544/197 |
| 0208376 | 1/1987 | European Pat. Off. | 544/197 |

Primary Examiner—Donald E. Czaja
Assistant Examiner—Carolyn Paden
Attorney, Agent, or Firm—Raymond D. Thompson

[57] ABSTRACT

Natural or synthetic fats are stabilized against oxidative and color degradation by the incorporation therein of new tris(N-alkyl-p-phenylene diamino)-1,3,5-triazine compounds.

20 Claims, No Drawings

STABILIZED FAT COMPOSITIONS

BACKGROUND OF THE INVENTION

This invention relates to the stabilization of fats and oils against oxidative degradation. More particularly, a fat containing unsaturation stabilized by a diarylamine substituted triazine compound.

A wide variety of naturally occurring oils and fats contain a mixture of olefinic compounds which vary in unsaturation and hence oxidizability from the singly unsaturated oleic to the polyconjugated eleostearic esters. Oxidation is the major cause of deterioration of edible oils and fats. Oxidative deterioration of domestic fats such as butter, margarine, lard and cooking oils and the foodstuffs into which they are incorporated, is manifested initially as loss of flavor. This is followed by rancidity due to the formation of aldehydes and acids which become increasingly toxic. Long before this state is reached, however, important minor constituents of the natural oils and fats such as the vitamins and some of the terpenoid flavoring constituents have been destroyed. Protection against the onset of rancidity is an ongoing desired objective in the food processing industry.

Aldehydes have been recognized for many years as the chemical agents responsible for rancidity. These products have been shown to be derived from initially formed hydroperoxide. The primary initial products of the autoxidation of fatty acid esters, the hydroperoxides, appear to be odorless and flavorless. However, a host of carbonyl compounds, acids, and other products are formed, through decomposition and further oxidation of the hydroperoxides. Many of the secondary products have relatively low molecular weights, and presumably all such compounds contribute to the off-flavors and odors.

Perhaps the principal objection, in many parts of the world, to rancidity in fat products has been an esthetic aversion to the rancid odor and flavor. People who become accustomed to the natural flavor and odor of fresh and carefully processed food materials acquire a distaste for any flavor and odor that can be associated with poor processing or long storage under unfavorable conditions.

A second, and fundamentally more important, basis for objecting to common oxidative rancidity is based on possible harmful effects that result from the consumption of oxidized fat. The extent to which rancid fat should be considered harmful continues to be a controversial question.

It may be said unequivocally that oxidized fats cause some destruction of certain fat-soluble vitamins and possibly other nutrients in the diet. In particular, it has been demonstrated that several fat-soluble vitamins and carotene are destroyed in oxidized fats.

Of the more efficient synthetic antioxidants which have been extensively tested in foodstuffs, the most important are mixed 2 and 5 tert.-butyl-4-methoxy phenols (BHA) and 2,5-di-tert.-butyl-4-methylphenol and a number of other antioxidants, including bis-phenols, amine antioxidants such as diphenyl-p-phenylene-diamine (DPPD) and 6-ethoxy-2,2,4-trimethyl-1,2-dihydroquinoline.

BRIEF DESCRIPTION OF THE INVENTION

The advantages of the invention may be obtained by incorporating into a fat an effective amount of a compound of the general formula:

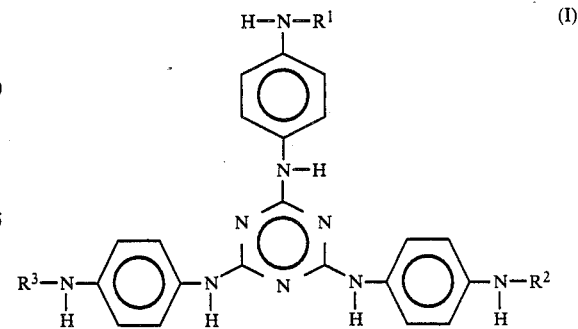

in which $R^1$, $R^2$ and $R^3$ are radicals independently selected from a $C_3$-$C_{18}$ branched or linear alkyl, or a $C_3$-$C_{12}$ cycloalkyl or a $C_3$-$C_{12}$ cycloalkyl substituted with one or more $C_1$-$C_{12}$ alkyl groups.

These compounds for use in the present invention may be prepared by a process of reacting an N-alkyl-p-phenylenediamine with a tri-halotriazine in a solvent to form a reaction mixture including a 2,4,6-tris(N-alkyl-p-phenylene)-1,3,5-triazine trihydrohalide; and neutralizing said 2,4,6-tris(N-alkyl-p-phenylenediamino)-1,3,5-triazine trihydrohalide with a base to form a 2,4,6-tris(N-alkyl-p-phenylenediamino)-1,3,5-triazine.

Unsaturated fats may be stabilized against rancidification by incorporation therein of an effective amount of the compounds of structure (I) along with optional costabilizers.

DETAILED DESCRIPTION OF THE INVENTION

The term "fat" as used herein can be naturally occurring or synthetically produced and meet any one of the following criteria:
1. It contains oleic acid.
2. It contains palmitic acid.
3. It contains mixtures of mixed triglycerides.
4. It contains $C_{14}$-$C_{18}$ saturated fat molecules and $C_{14}$-$C_{24}$ unsaturated fat molecules.

Specifically included are the fish meals made from ground fish, such as Peruvian Herring and fish oils (sardine, cod-liver, etc.). Fish meal is principally used as a protein and fat source for animal feeds, particularly as a component in poultry feed stocks. Fish meal is a broad term generally referring to the residue of ground fish (i.e., Herring) from which most of the water has been extracted. The fish meal contains, by weight, a majority of crude protein and minority components of oils, ash and residual moisture. The oil component is contained in the lipid extractibles. The lipids can be extracted using solvents such as chloroform, methanol, various ethers, light petroleum (40°–60° C. B.P.) etc.

Oleic acid (cis-octadec-9-enoic acid, $CH_3[CH_2]_7 \cdot CH:CH \cdot [CH_2]_7 \cdot COOH$) is undoubtedly the most widespread of all natural fatty acids; in very many fats it forms more than 30 per cent of the total fatty acids, and up to the present it has been found absent from no natural fat or phosphatide. The most common constituent of all natural fats is thus an unsaturated (mono-ethenoid), normal aliphatic acid with a content of eighteen carbon atoms and the unsaturated linking between the ninth and tenth carbon atoms of the chain. Many other unsaturated acids, mono- or poly-ethenoid, are also found in fats, and of these quite a number have features of chemical structure which bear similarity, close or remote, to that of oleic acid. Other unsaturated acids, however, seem to be quite different from oleic acid and its structurally related acids in the arrangement of their unsaturated linkages. None of the other unsaturated acids are so uniformly distributed, or so prominent as a whole, in natural fats as oleic acid; but two at least appear to be nearly as widespread, namely, octadeca-9,12-dienoic acid (linoleic acid or related forms),

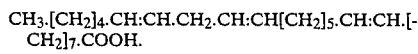

$CH_3.[CH_2]_4.CH:CH.CH_2.CH:CH[CH_2]_5.CH:CH.[CH_2]_7.COOH.$

Saturated normal aliphatic acids are, of course, widely distributed in natural fats. Here the characteristic member of the group is palmitic acid, $CH_3.[CH_2]_{14}.COOH$; this acid occurs in very many fats, in which it may contribute from 15 to 50 per cent of the total fatty acids like oleic acid, it is completely absent from few, if any, of the natural fats. The fatty acid mixtures are combined as triglycerides in fats from different regions of the vegetable and animal kingdoms. They are woven into molecules of triglycerides in vegetable or animal, "depot" (reserve) or "tissue" (organ) fat. Natural fats should be defined, in fact, as mixtures of mixed triglycerides.

The essential stabilizer of the invention is defined by structure (I).

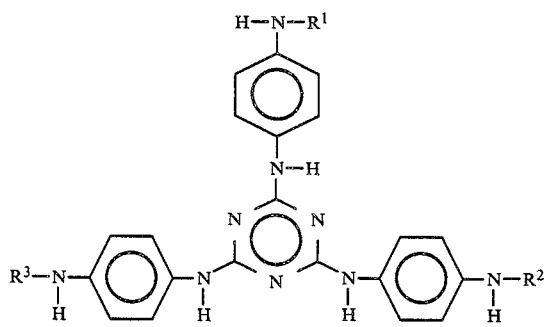

in which $R^1$, $R^2$ and $R^3$ are radicals independently selected from a $C_3-C_{18}$ branched or linear alkyl, or a $C_3-C_{12}$ cycloalkyl or a $C_3-C_{12}$ cycloalkyl substituted with one or more $C_{1-12}$ alkyl groups.

Referring now to the compound of structure (I), the preferred compositions are those in which $R^1$, $R^2$ and $R^3$ are linear or branched $C_{3-18}$ alkyl groups. The alkyl groups more preferred are those with a secondary carbon in the alpha position to the nitrogen. In this configuration, the antioxidant activity of the compound is believed to be enhanced. Therefore, the more preferred alkyl groups are branched chains which provide an alkyl substituent which is in accordance with this configuration. The cycloalkyl or $C_{1-12}$ alkyl substituted cycloalkyls provide such an alpha carbon configuration as well. The structure of formula I which is most preferred at this time are compounds in which R1, $R^2$ and $R^3$ are $C_{6-8}$ branched chain alkyl groups. Examples of some preferred stabilizers of Structure (I) useful in the present invention are: 2,4,6-tri(N-1,4-dimethylpentyl-p-phenylenediamino)-1,35-triazine; 2,4,6-tris(N-isopropyl-p-phenylenediamino)-1,3,5-triazine; 2,4,6-tris(N-cyclohexyl-p-phenylenediamino)-1,3,5-triazine, 2,4,6-tris(N-sec-butyl-p-phenylenediamino)-1,3,5-triazine; 2,4,6-tris(N-1,3-dimethylbutyl-p-phenylenediamino)-1,3,5-triazine; 2,4,6-tris(N-1-methylheptyl-p-phenylenediamino)-1,3,5-triazine; 2,4,6-tris(N-2,4-di-tert-butylcyclohexyl-p-phenylenediamino)-1,3,5-triazine; 2,4,6-tris(N-2-sec-butylcyclohexyl-p-phenylenediamino)-1,3,5-triazine, 2,4,6-tris(1-methyldecyl-p-phenylenediamine)-1,3,5-triazine. The most preferred material 2,4,6-tris(N-1,4-dimethylpentyl-p-phenylenediamino)-1,3,5-triazine.

The primary stabilizer of structure (I) may be optionally combined with other materials known to be useful as antioxidants. These optional additives are described herein as costabilizers. Particularly preferred are those conventionally used in food products such as: BHT; BHA; citric acid; vitamins A, C, D, and E; other tocopherols and beta-carotenes. Synergists such as ascorbic acid; phospholipids, lecithin, gallate esters, such as lauryl gallate and propylene gallate, thiodipropionic acid, dilaurylthiodiproprionate, dioctadecylthiodipropionate, monoisopropyl citrate, stearyl citrate, and gum guaial are also used selectively in food products around the world.

The stabilizer compounds for the invention can be synthesized advantageously by the following general method. Although the reagents may be added in different order as shown in some of the examples, the preferred method is as follows:

The N-alkyl-p-phenylenediamine, which is prepared by methods known to those familiar with the art, is reacted with 2,4,6-tri-halogeno-1,3,5-triazine. A molar equivalent of the preferred tri-halo triazine commonly called cyanuric chloride is added as a powder to a solution of three plus moles of the N-alkyl-p-phenylene diamine in a suitable solvent such as isopropanol, at ambient temperatures with appropriate cooling. The first two halogen atoms are displaced rapidly. The reaction mixture is then heated to 60°–80° C. in order to complete the displacement of the third halogen atom. After 4–5 hours heating at 60°–80° C. the formation of the 2,4,6-tris-(N-alkyl-p-phenylenediamino)1,3,5-triazine trihydrochloride is complete.

The process is unique in that the basicity of the alkyl-p-phenylenediamine allows the displaced halogen atom of the cyanuric halide to form the hydrohalide directly thereby enabling isolation of the trihalide and effecting a purification step.

The tris-hydrochloride may be removed by filtration, then reslurried in a suitable water miscible solvent, neutralized with aqueous base such as sodium hydroxide, and crystallized from the aqueous solvent mixture.

If the starting N-alkyl-p-phenylene diamine is sufficiently pure, or a less pure product is acceptable, isolation of the tris-hydrochloride is not necessary, and the reaction mixture can be neutralized and the product crystallized and isolated by filtration.

Temperature control of the reaction is of some importance. It is preferred that the first stage of the reaction take place below 30° C. and that the second stage take place at least 30° C. above the first stage. Selection of the optimal temperatures are, of course, dependent upon the identity of the p-phenylene diamine and solvent which is chosen.

Preferred solvents are alcohols although any suitable solvent may be utilized. The term solvent is meant to include an excess of the N-alkyl-p-phenylenediamine which may serve to solvate the reaction product and allow subsequent isolation.

It is noted here that any use of the term "alkyl", in the context of a starting material (i.e., N-alkyl-p-phenylene diamine) of the final substituted triazine compounds of this invention, is deemed to include cycloalkyl and alkyl substituted cycloalkyl structures as well.

The triazine compounds (I) of the invention may be synthesized by a suitable synthesis route. The following synthesis examples are provided to illustrate a currently preferred method of manufacturing certain of the class of triazine compounds of the invention.

STABILIZER SYNTHESIS EXAMPLES

EXAMPLE 1:

2,4,6,-tris(N-1,4-dimethylpentyl-p-phenylene diamino)-1,3,5-triazine

In a 3-liter, four-necked, round-bottomed flask equipped with a thermometer, a mechanical stirrer, a condenser, and a dropping funnel was placed 1500 ml of isopropanol. The isopropanol was cooled to −10° C. and 184.4 grams (1 mole) of cyanuric chloride was added. To this stirred suspension was added 680 grams (3.3 moles) of 4-amino-N-(1,4-dimethylpentyl)aniline dropwise over 1 hour period keeping the temperature between −10 and −5° C. Over 1 hour the reaction mixture was warmed to 30° C. then held for 16 hours at 30° C. The reaction mixture was refluxed for 1 hour at about 80° C. The reaction was followed by high pressure liquid chromatograph by observing the disappearance of the starting amine, and the conversion of the intermediate mono- and bis- substituted compounds to the final tris-substituted product. After cooling to 60° C. 240 grams (3 moles) of 50 percent sodium hydroxide solution was added dropwise over 1 hour period. The sodium chloride was removed by filtration at 40° C. The filtrate was cooled to 10° C. and the solvent was decanted off. The oily lower layer was extracted with water at 60° C. then crystallized from fresh isopropanol. The total compound was recrystallized from hexane and it melted at 128-132° C. The yield was 78.1 percent. The infrared spectrum was consistent with the structure. Relative area HPLC analysis of the product showed it to be 95.8 percent pure.

EXAMPLE 2:

2,4,6-tris(N-isopropyl-p-phenylene diamino)1,3,5-triazine

In a 2 liter, four-necked, round-bottomed flask equipped with a thermometer, a mechanical stirrer, a condenser, and a dropping funnel was placed 650 ml. of isopropanol. The isopropanol was cooled to −5° C. and 36.8 grams (.2 mole) of cyanuric chloride was added. To this stirred suspension was added a solution of 90 grams (.06 mole) of 4-amino-N-isopropylaniline in 100 ml. of isopropanol dropwise over 1 hour period keeping the temperature between −05° and 0° C. Over ½ hour the reaction mixture was warmed to 30° C. then refluxed for 2 hours. The reaction was followed by high pressure liquid chromatography by observing the disappearance of the starting amine, and the conversion of the intermediate mono- and bis-substituted compounds to the final tris-substituted product. The reaction mixture was cooled, and allowed to stand overnight. The amine hydrochloride salt was neutralized by adding 96 grams (.6 mole) of 25 percent sodium hydroxide solution over ½ hour period, and then refluxing the mixture for ½ hour. The title compound precipitated upon cooling and was isolated by filtration, washed with isopropanol and hot water (60° C.), M.P. 196°-198° C. The yield was 75.2 percent. The infrared spectrum was consistent with the structure. Relative area HPLC analysis of the product showed it to be 95.3 percent pure.

RANCIDITY TESTING Determination of Peroxide Number

The antioxidation properties of a chemical are determined by the change in the peroxide number of the fat sample. The peroxide number of the fresh untreated fat sample should be under 5. The technique is an iodometric titration which is carried out as follows:

1. Take a 5 gram sample of fat (6 ml. of melted fat) and place in a 250 ml. iodine flask.
2. Add 30 ml. of a mixture of 60% acetic acid and 40% chloroform. (Dissolves fat).
3. Shake the flask until the solution becomes clear.
4. Add 0.5 ml. of saturated potassium iodide in 250 ml. flask. The peroxide in the fat oxidizes the iodide to iodine. Saturated potassium iodide solution is obtained by adding potassium iodide to small amount of distilled water until some settles in flask after shaking.
5. Add 0.5 ml. starch indicator solution. Shake well. To prepare the starch indicator solution, a paste containing 5 grams of starch, 5 grams of potassium iodide and 50 ml. of water is added to 450 ml. of boiling water. The cooled solution is then used as described below.
6. Wait 2 minutes and add 30 ml. of boiled, distilled water. Shake well.
7. Titrate to starch end point with 0.01N solution of sodium thiosulfate. Shake vigorously while titrating. Test is run for 1, 2, 3, 4, 6, 8 and 10 weeks.
8. The peroxide number per 100 grams of fat equals:

$$\frac{ml. \times n \text{ (sodium thiosulfate)} \times 1000}{\text{Sample Weight}}$$

Testing Procedure

1. A 150-gram sample of melted fat (water bath) is mixed with the test chemical in a 6" petri dish.
2. The treated fat is placed in an air oven at a temperature of 60° C.
3. After a zero time determination, the fat is titrated 1, 2, 4 and 8, etc., weeks after treatment until breakdown, which in our test equals a peroxide number of 30 or the test termination at 10 weeks.

RESULTS

The fat is considered rancid when the peroxide number exceeds 30. The greater than antioxidant properties of the chemical the longer the fat takes to become rancid. The color of the fat was subjectively observed at the end of the rancidity test to record undesirable color changes in the test specimens.

| TABLE OF RESULTS Peroxide Number per 100 grams of Fat | | |
|---|---|---|
| Stabilizer Identity | Example 1* | Control** |
| Additive Level | 100 ppm | 100 ppm |
| Unaged Peroxide # | .23 | .40 |
| Days | | |

-continued

| TABLE OF RESULTS Peroxide Number per 100 grams of Fat | | | | |
|---|---|---|---|---|
| Stabilizer Identity | Example 1* | | Control** | |
| Additive Level | 100 ppm | | 100 ppm | |
| Unaged Peroxide # | .23 | | .40 | |
| 6 | 1.8 | 2.2 | .5 | .6 |
| 13 | 1.7 | 2.3 | 1.0 | 1.1 |
| 21 | 1.9 | 1.9 | 1.5 | 1.6 |
| 27 | 1.7 | 2.0 | 1.9 | 1.8 |
| 35 | 1.8 | 1.7 | 1.6 | 2.0 |
| 52 | 1.8 | 2.0 | 3.0 | 5.7 |
| 59 | 2.3 | 2.5 | 4.0 | 4.4 |
| 69 | 4.0 | 4.5 | 5.2 | 5.2 |
| Color | Off-White | | Bright Orange | |

*2,4,6-tris(N—1,4 dimethylpentyl-p-phenylenediamino)-1,3,5 triazine. Specie of Structure (I).
**N,N'—diphenylparaphenylenediamine.

As can be seen in the Table of Results the fat solubilized by a species of Structure (I) demonstrates excellent ability to postpone the onset of rancidity. It also showed much better color stability in the aged fat compared to the closest known amine control material, DPPD, also known as Naugard⊥ J available from Uniroyal Chemical Company, Inc., and trademarked by the same company.

COMMERCIAL APPLICABILITY

This color improvement was a completely unexpected result which may translate to much better color and rancidity stability for fats used for deep frying of fast foods. In addition, fish meal, which is used as a component of poultry feeds, can greatly benefit from improved oxidative stability during shipping from the country of origin, such as Peru, to the consuming country, such as the United States.

Various modification to the invention can be made without departing from the intended scope of the invention as set forth in the claims.

What is claimed is:

1. A stabilized fat composition comprising a fat having incorporated therein an antioxidatively effective amount of a compound of the general formula:

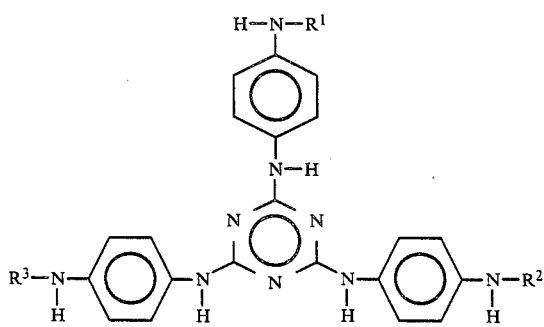

in which $R^1$, $R^2$ and $R^3$ are radicals independently selected form a $C_{3-18}$ branched or linear alkyl, or a $C_{3-12}$ cycloalkyl substituted with one or more $C_{3-12}$ alkyl groups.

2. A stabilized fat composition according to claim 1 wherein said $R^1$, $R^2$ and $R^3$ are the same radicals in said compound (I).

3. A stabilized fat composition according to claim 1 wherein $R^1$, $R^2$ and $R^3$ are the same radical selected from $C_{3-18}$ branched alkyl radicals.

4. The stabilized fat composition according to claim 3 wherein $R^1$, $R^2$ and $R^3$ are $C_{6-8}$ secondary alkyl radicals.

5. A stabilized fat composition according to claim 1 wherein the radicals have a secondary carbon atom in the alpha position relative to the nitrogen.

6. A stabilized fat composition according to claim 2 wherein $R^1$, $R^2$, and $R^3$ are 1,4-dimethylpentyl radicals.

7. A stabilized fat composition comprising a fat having incorporated therein an antioxidatively effective amount of A 2,4,6-tris(N-alkyl-p-phenylenediamino)-1,35-triazine stabilized fat composition in which the alkyl radical is selected from a $C_{3-18}$ branched or linear alkyl, or a $C_{3-12}$ cycloalkyl or a $C_{3-12}$ cycloalkyl substituted with one or more $C_{1-12}$ alkyl groups.

8. The stabilized fat composition according to claim 7 wherein the alkyl is selected from the group consisting of 1,4-dimethylpentyl; isopropyl; cyclohexyl; sec-butyl; 1,3-dimethylbutyl; 1-methylheptyl; 2,4-di-t-butylcyclohexyl; 2-sec-butylcyclohexyl; and 1-methyldecyl.

9. The stabilized fat composition according to claim 7 wherein the alkyl is 1,4-dimethylpentyl.

10. The stabilized fat composition according to claim 7 wherein said stabilized fat composition is 2,4,6-tris-(N-1,4-dimethylpentyl-p-phenylenediamino)-1,3,5-triazine.

11. The stabilized fat composition according to claim 7 wherein said stabilized fat composition is 2,4,6-tris(N-1,3-dimethylbutyl-p-phenylenediamino)-1,3,5-triazine.

12. The stabilized fat composition according to claim 7 wherein said stabilized fat composition is 2,4,5-tris(N-1-methylheptyl-p-phenylenediamino)1,3,5-triazine.

13. The stabilized fat composition according to claim 7 wherein said stabilized fat composition is 2,4,5-tris(N-sec-butyl-p-phenylene diamino)-1,3,5-triazine.

14. A stabilized fat composition according to claim 1 wherein said fat contains at least one fatty acid selected from the group consisting of oleic, palmitic and linoleic acids.

15. A stabilized fat composition according to claim 1 wherein said fat contains mixtures of triglycerides.

16. The stabilized fat composition according to claim 1 wherein said fat contains $C_{14}$ to $C_{24}$ unsaturated fat molecules.

17. A stabilized fat composition according to claim 16 wherein said fat contains $C_{14}$ to $C_{18}$ saturated fat molecules.

18. A stabilized fat composition according to claim 1 wherein said fat forms a portion of a fish meal composition.

19. A stabilized fat composition according to claim 1 further comprising a costabilizer selected from the group consisting of citric acid, ascorbic acid, tocopherols compounds, lecithin and gallate ester compounds.

20. An oxidatively stable fish meal composition comprising:

(a) fish meal containing at least one unsaturated fat; and (b) a stabilizer of structure (I), added in an antioxidatively effective amount to said fish meal,

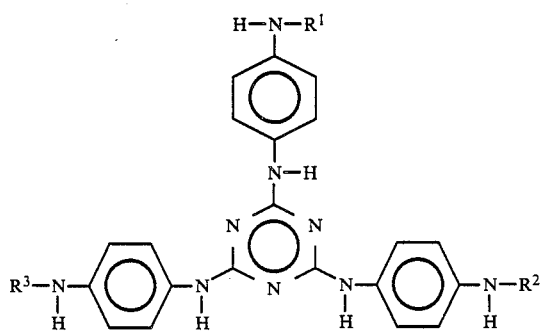

(I)

in which $R^1$, $R^2$ and $R^3$ are radicals independently selected from a $C_{3-18}$ branched or linear alkyl, or a $C_{3-12}$ cycloalkyl or a $C_{3-12}$ cycloalkyl substituted with one or more $C_{1-12}$ alkyl groups.

\* \* \* \* \*

(I)

in which $R^1$, $R^2$ and $R^3$ are radicals independently selected from a $C_{3-18}$ branched or linear alkyl, or a $C_{3-12}$ cycloalkyl or a $C_{3-12}$ cycloalkyl substituted with one or more $C_{1-12}$ alkyl groups.

\* \* \* \* \*